United States Patent [19]
Hofeldt

[11] Patent Number: 5,347,330
[45] Date of Patent: Sep. 13, 1994

[54] SYSTEM AND METHOD USING THE PULFRICH STEREO-ILLUSION PHENOMENON TO SCREEN EYES AND DETECT OCULAR AND OPTIC NERVE DISEASE

[76] Inventor: Albert J. Hofeldt, 200 E. 57th St., New York, N.Y. 10022

[21] Appl. No.: 61,966

[22] Filed: May 14, 1993

[51] Int. Cl.⁵ .................... A61B 3/02; A61B 3/032
[52] U.S. Cl. .................... 351/223; 351/234; 351/240; 351/246; 128/745
[58] Field of Search ............. 359/478, 479; 128/745; 358/3, 88, 89; 351/200, 201, 222, 223, 233, 234, 237, 240, 246; 348/44, 78

[56] References Cited

U.S. PATENT DOCUMENTS

| | | | |
|---|---|---|---|
| 4,131,342 | 12/1978 | Dudley | 358/88 X |
| 4,705,371 | 11/1987 | Beard | 359/465 X |
| 5,026,151 | 6/1991 | Waltuck et al. | 351/201 X |
| 5,099,858 | 3/1992 | Hofeldt | 128/745 |
| 5,144,344 | 9/1992 | Takahashi et al. | 351/44 |

Primary Examiner—William L. Sikes
Assistant Examiner—David R. Parsons
Attorney, Agent, or Firm—Rosenman & Colin

[57] ABSTRACT

A simple and relatively inexpensive system has been developed for screening people both with normal vision and those with ocular and optic nerve disease using the Pulfrich stereo-illusion phenomenon. The system uses an audio/visual recording showing a ballerina moving in a pendulum fashion in front of a cone. The person to be tested uses a device which sequentially has no filters and filters of varying density whereby the patient with normal vision will see the ballerina moving back and forth in front of the cone and then rotating around the cone clockwise and counter-clockwise. The audio/visual recording may be shown to the person to be tested on a television set or a tv monitor.

12 Claims, 2 Drawing Sheets

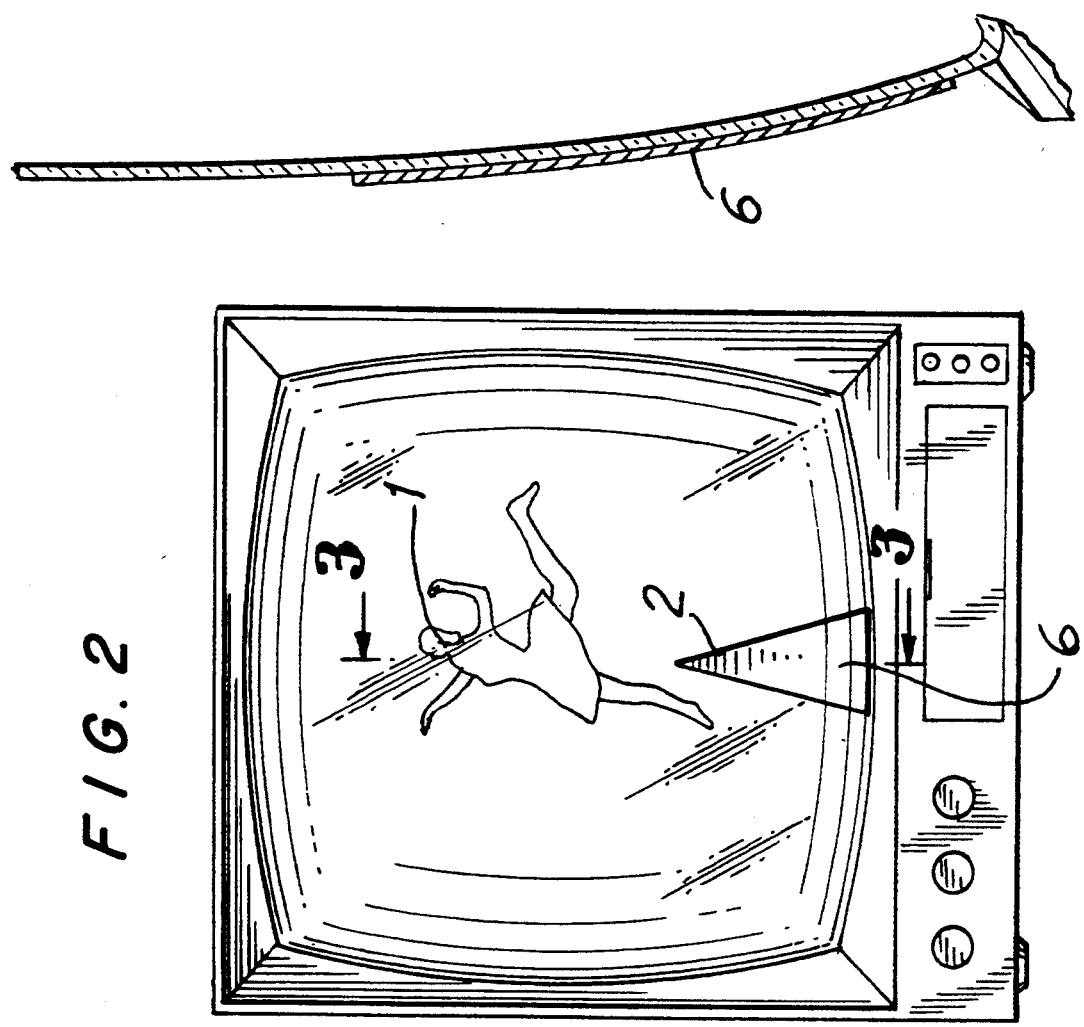

SYSTEM AND METHOD USING THE PULFRICH STEREO-ILLUSION PHENOMENON TO SCREEN EYES AND DETECT OCULAR AND OPTIC NERVE DISEASE

BACKGROUND OF THE INVENTION

Miriam L. Schmitt U.S. Pat. No. 5,099,858 (which is incorporated herein by reference), I described and claimed a device useful for measuring the Pulfrich stereo-illusion phenomenon in people with normal vision and without ocular and optic nerve disease and for diagnosing ocular and optic nerve disease in people who are capable of experiencing that phenomenon. I also described and claimed a method of measurement utilizing my novel device.

My present invention is a further advance in technology and resides in making a video recording comprising a series of repeating segments, each segment showing the ballerina and cone as described in my issued patent. The person to be tested views the video and follows the audio instructions. Data is recorded and the measurements are assessed by an ophthalmologist to determine the condition of the eyes of the person being tested. When the video is shown on a television receiver or monitor, the accuracy of the measurements are greatly enhanced by superimposing a cone on the exterior viewing surface over the cone as it is shown in the recorded segments.

The Pulfrich stereo-illusion is a psychophysical response dependent on stereoscopic binocular central vision. The Pulfrich stereo-illusion phenomenon of a frontal plane oscillating object appearing to travel in an elliptical orbit when viewed with unequal binocular illumination was described in 1922 by Carl Von Pulfrich, a German scientist. Viewed from above, the direction of the orbit is clockwise when the image perceived by the left eye is dimmer and counter-clockwise when the image perceived by the right eye is dimmer. The apparent depth of the orbit has been found to vary the difference in the binocular retinal illumination, and the distance from the observer to the pendulum bob, and inversely with the background illumination level.

Pulfrich postulated that the stereo effect resulted from a prolonged latent period of vision along the afferent pathway of the eye perceiving the dimmer image. Subsequent investigators using the episcotistor, random dot stereo-movies, and visual-evoked responses, have confirmed that the latent period of vision increases as the retinal illumination decreases. The synchronous conduction of impulses originating from corresponding retinal points produces disparity in the simultaneous perception of these stereo-pairs and hence the false sensation of depth to the viewer.

The minimum visual and stereoscopic acuities required to appreciate the normal stereo-illusion were first described by me in "Clinical Applications of the Pulfrich Phenomenon" in Ocular Inflammation Ther. 1:117–123 (1983) and in my EPA 87402784.0 published Jun. 15, 1988.

It has been suggested in the literature that the appreciation of the Pulfrich stereo-illusion depends not only on normal vision, but also upon the skill of the individual as an observer. Consequently, the inability to induce the normal stereo-illusion by placing a filter before one eye has not been considered a sign of disease since factors other than visual acuity and stereopsis have been thought to influence the appreciation of the stereo-illusion. However, using my device, I have shown that all normal sighted persons are able to see the stereo-illusion under the testing conditions described in my U.S. Pat. No. 5,099,858.

Utilizing the Pulfrich stereo-illusion, I developed a device I call the stereo-photometer for determining the presence of diseases affecting the visual system which interferes with central acuity, stereopsis, or the brightness equality of the images perceived by the right and left visual pathways. This has been described and claimed in my U.S. Pat. No. 5,099,858. Reduced perceived brightness can be the result of pre-retinal, retinal, or optic nerve disease. Regardless of the anatomical site responsible for the brightness imbalance of the right and left visual pathways, the correct neutral density filter positioned before the eye perceiving the brighter image will bring the right and left visual pathways into balance. In the development of the stereo-photometer, I have applied the Pulfrich stereo-illusion principle as a sensitive brightness balance to compare and measure the visual input to the right and left visual pathways. The stereo-photometer is designed to precisely control and measure the luminance to each eye with variable neutral density filters while maintaining constant all other variables known to affect the stereo-illusion. The luminance difference between the two eyes (interocular) can be calculated from the measured luminance to each eye.

The stereo-illusion is a normal phenomenon only when occurring within a certain range of interocular luminance differences. A disease of the visual system is present when: (1) the stereo-illusion is seen by the subject without attenuating the luminance to either eye (spontaneous response), (2) the luminance attenuation to induce the stereo-illusion is different for each eye and outside the normal range (asymmetric induced response), (3) the luminance attenuation to neutralize an induced stereo-illusion created with a standard value neutral density filter is different for each eye and outside the normal range (asymmetric neutralization response), (4) a subthreshold neutral density filter placed before one but not the other eye induces the stereo-illusion, or (5) the stereo-illusion cannot be induced at any interocular luminance difference (non-inducible response).

The spontaneous response has a specific orientation which dictates the pathway perceiving the dimmer image, i.e., clockwise for the left pathway and counter-clockwise for the right pathway. Testing with the stereo-photometer, the spontaneous response can be precisely quantitated by balancing the brightness disparity between the right and left visual pathways with the progressive neutral density filter before the eye perceiving the brighter image until the endpoint is reached. The endpoint is the moment the pendulum bob motion changes from rotational about a reference point to planar.

The spontaneous response is seen by the person without altering the ambient viewing conditions and occurs when the brightness disparity between the right and left visual pathways exceed a threshold difference. This happens in pre-retinal diseases causing unequal pupils of media opacities, retinal diseases causing neuronal dysfunction within the retina, or optic nerve disease causing delay nerve conduction velocity as I reported in "Clinical Application of the Pulfrich Phenomenon," Ocular Inflammation Ther. 1:117–123 (1983) and "Pulfrich Stereo-Illusion Phenomenon in Serous Sensory Retinal Detachment of the Macula," Amer. J. Ophthalmol. 100:576–580 (1985) and in my EPA 87402784.0, published Jun. 15, 1988.

Disease conditions exist in which the brightness appreciation is less in one visual pathway than the other but not to the degree that produces the spontaneous response. This subthreshold brightness disparity can be detected by the induction or neutralization technique. If the brightness appreciation is unequal for the two sides, the induction or neutralization endpoints will be different for each side and the larger the interocular difference the more the brightness disparity. An alternative induction technique to detect a subthreshold brightness defect is to use a neutral density filter of less density than required to induce the stereo-illusion in normal sighted people. Placing this sub-threshold filter before the eye with the subthreshold defect the combination will result in an interocular difference of the threshold level for the stereo-illusion. When this same subthreshold filter is placed before the opposite eye, threshold level cannot be reached since that eye must be functioning at a high relative brightness level and would require a filter of higher density than required to induce the stereo-illusion in a normal sighted person.

The use of a cone as the reference point and a ballerina is important in maximizing the stereo-illusion effect for the observer.

I discovered that a cone is a particularly useful fixation target and that a ballerina is a familiar and pleasant object for the observer. The ballerina is positioned so that one extended leg overlaps the conical fixation target. The colors of the overlapping areas are different to allow easy spacial recognition but similar enough to reduce visual clues of the actual planar movement of the ballerina during the observation of the stereo-illusion. In one embodiment the extended leg of the ballerina is black and overlaps a lilac portion of the cone and the skirt of the ballerina is lilac and overlaps the black tip of the cone.

SUMMARY OF THE INVENTION

According to my present invention, a multiplicity of segments are recorded on a video cassette. Each segment which lasts approximately one minute and shows the ballerina 1 moving back and forth in a pendulum type movement with one extended leg of the ballerina overlapping a portion of the cone 2. An audio track instructs the person to be tested to view the moving ballerina through two eye pieces 3 which contain a plurality of filters which vary the amount of light transmitted to each of the eyes of the person to be tested.

The eye pieces 3 contain no lenses or clear lenses as well as filters so that the person with normal vision would first view the ballerina moving back and forth behind the cone and then as instructed by the audio portion as each filter is in turn used, the patient would then experience the ballerina rotating in either a counter-clockwise or a clockwise direction and, following that with the next filter in the opposite circular direction. The next lenses would be clear and the procedure would be repeated at least 2 times in each recorded segment.

While it is preferable that an ophthalmologist or an experienced tester would record when the person sees the ballerina moving in a pendulum fashion back and forth behind the cone, when the person sees the ballerina rotating clockwise around the cone, when the person sees the ballerina rotating counter-clockwise around the cone and then in a pendulum motion again, it is possible using the audio instructions to instruct the person to be tested to record the results for later analysis by the ophthalmologist.

The recordation may be accomplished by any suitable means such as providing a sheet of paper on which to record the results or by the patient orally saying to the one recording the results what he or she then sees.

Filters of the type described in my U.S. Pat. No. 5,099,858 can be utilized and suitably a viewing device 4 having eye pieces and containing filters such as wheel 5 may be given to the person to be tested.

According to my present invention fixed time segments preferably of about one minute each are recorded and at least five are combined on a video recording. Five to ten segments are sufficient to provide accurate reproducible measurements.

More particularly, according to my present invention as shown in the drawings, a recording is played back over a television receiver or monitor. The recording contains a plurality of segments preferably five to ten, each of which lasts approximately one minute. Each segment is identical and shows the ballerina 1 moving in a pendulum motion in front of cone 2 at a fixed rate of movement for each period of time. The person to be tested is instructed by the audio portion of the recording to look through a viewing device 4 which contains filters 5 as described in my U.S. Pat. No. 5,099,858 and to record either himself or herself or by informing the tester when the ballerina changes from a pendulum motion to a counter-clockwise or clockwise movement. It has been found that more accurate measurements are obtained when a cone or triangle 6 is placed on the exterior viewing surface of the television receiver or monitor and is superimposed over the cone 2 as shown in the prerecorded segments.

Most conveniently, the filters are contained in a readily portable device having means for changing the filters through which the person's eyes see the ballerina and cone in a pre-determined sequence.

The audio portion of the recording instructs the patient when to go to the next pair of filters. The tester than compares the results with a standard for people with normal vision.

BRIEF DESCRIPTION OF THE DRAWINGS

With reference to the drawings, FIG. 1 shows a television receiver or monitor showing a recorded segment of the ballerina in movement behind a cone.

FIG. 2 is a front view of a television receiver or monitor having a cone 6 disposed on the exterior surface superimposed over cone 2.

FIG. 3 is a sectional view taken along lines 2—2 of FIG. 2 and shows a cone superimposed on the exterior viewing surface of the television receiver or monitor so that it is superimposed over the cone as shown during the recorded segment.

DETAILED DESCRIPTION OF THE INVENTION

Figure 4:
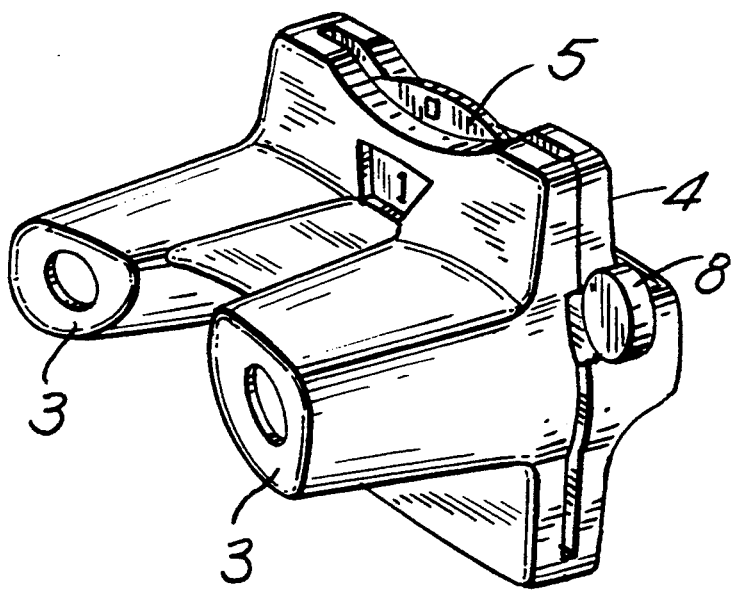
FIG. 4 shows a suitable viewing device which contains a circular array of neutral density filters.
Figure 5:
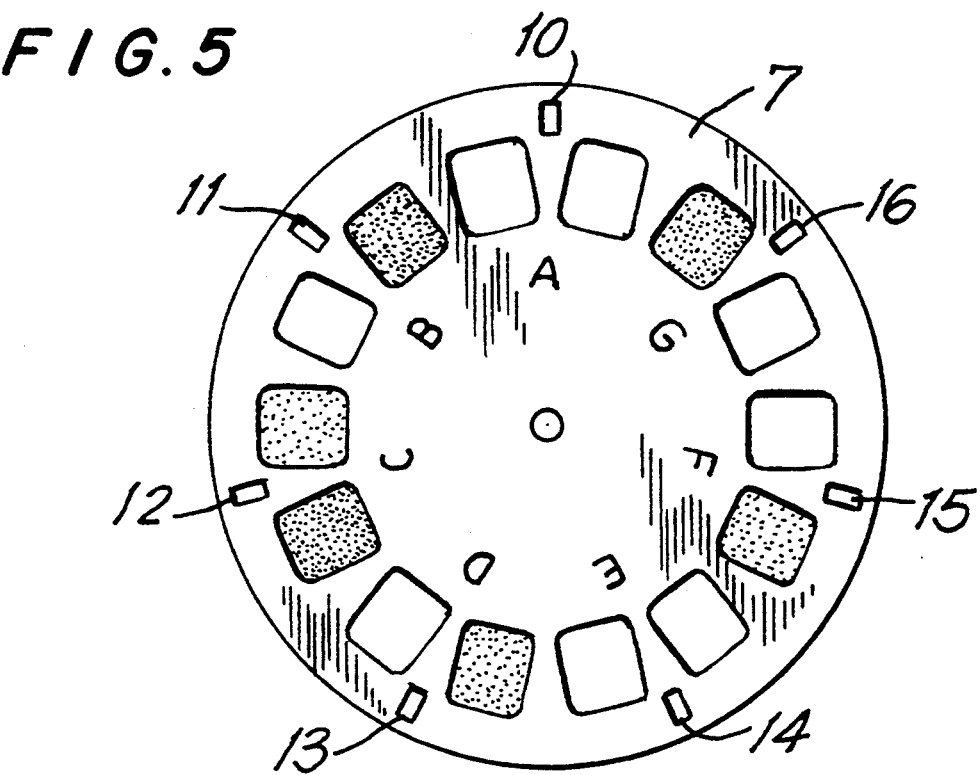
FIG. 5 shows a filter wheel for use in the device of FIG. 4.

In order to see the stereo illusion 20/60 or better acuity in each eye and stereopsis of at least 3000 seconds of arc are required.

My present invention is capable of achieving all of the advantages as set forth for the device described and claimed in my U.S. Pat. No. 5,099,858 but is more readily useful for simple and inexpensive testing and screening of patients as well as for mass testing and screening of patients.

According to one embodiment of my invention the recording is played back over a television receiver or monitor and the person to be tested places a viewing device such as 4 having eye pieces 3 before him. The device contains a series of filters 7 of different density contoured, for example, together with openings on filter wheel 5. The person to be tested would begin by looking through both open spaces A with both eyes. Next, the person would move the filter wheel 5 to point B which contains a filter for the right eye and an opening for the left eye. Following that, the person would move to C which contains a filter for both eyes of different density. Next, the person would move to point D on the filter wheel, which has an opening through which the right eye would look and a filter through which the left eye looks. Then the person would move to point E where both eyes look through open spaces. Next the person moves to point F where the right eye looks G is the last point on the wheel sequence where the right eye looks through an opening and the left eye looks through a filter. The next sequence is then a repetition of movement through openings and filters A–G.

The filter wheel 7 may be moved from points A–G by arm 8 through a racket or similar mechanism whereby an element moves from spaces 10 to 16 as arm 8 is moved.

What is claimed is:

1. A system for measuring the Pulfrich stereo-illusion phenomenon in people with normal vision and without ocular and optic nerve disease, and for diagnosing ocular and optic nerve diseases in people who are incapable or capable of experiencing the Pulfrich stereo-illusion phenomenon, which comprises two eye pieces, an audio-visual recording, a device capable of showing and playing the recording to a person to be measured, and means for making a record of the results measured, wherein the recording shows a ballerina moving in a pendulum motion behind a reference point which comprises a cone, and wherein the eye pieces have means for diminishing the amount of light received by each eye, and said means for making a record of the results measured comprises recording when the person to be measured sees the ballerina moving in a pendulum motion back and forth behind the reference point and whether or not the person to be measured also sees the ballerina rotating around the cone in either a clockwise or counter-clockwise direction as the amount of light perceived by each eye in turn is varied by means of the two eye pieces.

2. A system according to claim 1 wherein the two eye pieces are contained in a single unit which has means for varying the amount of light perceived by each eye in turn in a manner enabling those who are capable of experiencing the Pulfrich stereo-illusion phenomenon to so observe it when viewing the recording.

3. A system according to claim 2 wherein the device capable of showing the recording comprises a television monitor or receiver having means for showing and playing an audio-visual recording to a person to be measured.

4. A system according to claim 3 wherein the monitor or receiver has a triangle affixed to the outer viewing surface thereof which is superimposed upon the cone displayed during the course of showing or playing the recording.

5. A system according to claim 1 wherein the recording comprises at least five repeating segments.

6. A method of measuring the Pulfrich stereo-illusion phenomenon in people with normal vision and without ocular and optic nerve disease, and for diagnosing ocular and optic nerve disease in people who are incapable or capable of experiencing the Pulfrich stereo-illusion phenomenon, which comprises positioning a person to be measured in front of a device capable of showing and playing an audio-visual recording to the person to be measured, providing the person to be measured two eye pieces capable of varying the amount of light perceived through each of the eyes of the person to be measured, and playing an audio-visual recording to the person to be measured which shows a ballerina moving in a pendulum motion slightly behind a cone, instructing the person to be measured to vary the amount of light perceived through each eye, making a record of or having the person record whether the person's perception of the ballerina is one of a pendulum motion behind the cone or whether the ballerina is perceived as encircling the tip of the cone either clockwise or counter-clockwise, repeating the procedure for at least one additional replication, and making a record of or having the person record the results.

7. A method according to claim 6 wherein the device comprises a television monitor or a receiver.

8. A method according to claim 7 wherein the television monitor or receiver has a triangle on its outer viewing surface superimposed over the cone as during the course of the playing of each recorded segment.

9. A method according to claim 8 wherein the two eye pieces are in a single unit which contains a series of pairs of filters preventing different amounts of light to be received by each eye.

10. A method according to claim 6 wherein the two eye pieces are contained in a single unit which has means for varying the amount of light perceived by each eye in turn in a manner enabling those who are capable of experiencing the Pulfrich stereo-illusion phenomenon to so observe it when viewing the recording.

11. A method according to claim 10 wherein the person to be measured views at least two repeating segments and the results are recorded.

12. A method according to claim 10 wherein the person to be measured views at least five repeating segments and the results are recorded.

* * * * *